United States Patent
Mallard et al.

(10) Patent No.: US 10,959,934 B2
(45) Date of Patent: *Mar. 30, 2021

(54) MICRO- OR NANOPARTICULAR VESICLES COMPRISING CROSSLINKED HYALURONIC ACID, COMPOSITIONS COMPRISING THE SAME AND METHOD FOR THEIR USE IN SKIN CARE

(71) Applicant: NESTLÉ SKIN HEALTH S.A., Lausanne (CH)

(72) Inventors: Claire Mallard, Mougins (FR); Yves Rival, Antibes (FR)

(73) Assignee: GALDERMA HOLDING SA, La Tour-de-Peilz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/453,808

(22) Filed: Jun. 26, 2019

(65) Prior Publication Data

US 2019/0314262 A1 Oct. 17, 2019

Related U.S. Application Data

(63) Continuation of application No. PCT/EP2017/084760, filed on Dec. 28, 2017.

(30) Foreign Application Priority Data

Dec. 29, 2016 (EP) .................................... 16306846

(51) Int. Cl.
| | | |
|---|---|---|
| *A61K 31/728* | (2006.01) | |
| *A61K 8/73* | (2006.01) | |
| *A61K 8/14* | (2006.01) | |
| *A61K 8/37* | (2006.01) | |
| *A61Q 19/08* | (2006.01) | |

(52) U.S. Cl.
CPC ............. *A61K 8/735* (2013.01); *A61K 8/14* (2013.01); *A61K 8/37* (2013.01); *A61Q 19/08* (2013.01)

(58) Field of Classification Search
CPC . A61K 8/735; A61K 8/37; A61K 8/14; A61Q 19/08
USPC .......................................................... 514/54
See application file for complete search history.

(56) References Cited

U.S. PATENT DOCUMENTS

| | | | | |
|---|---|---|---|---|
| 5,019,174 A | * | 5/1991 | Wallach | A61K 8/14 |
| | | | | 134/40 |
| 5,830,499 A | | 11/1998 | Bouwstra | |
| 5,908,697 A | * | 6/1999 | Roux | A61K 9/1272 |
| | | | | 428/402.2 |
| 2007/0172442 A1 | | 7/2007 | Saurat et al. | |
| 2013/0274221 A1 | | 10/2013 | Paufique | |
| 2014/0039061 A1 | * | 2/2014 | Wiebensjo | A61K 47/61 |
| | | | | 514/626 |
| 2015/0174033 A1 | | 6/2015 | Herrmann et al. | |
| 2015/0272851 A1 | | 10/2015 | Bourdon et al. | |
| 2015/0306022 A1 | | 10/2015 | Chevreau | |
| 2017/0151538 A1 | | 6/2017 | Balooch et al. | |

FOREIGN PATENT DOCUMENTS

| | | |
|---|---|---|
| EP | 0 531 978 A2 | 3/1993 |
| FR | 2771635 A1 | 6/1999 |
| FR | 2939317 A1 | 6/2010 |
| WO | WO-2004/058796 A1 | 7/2004 |
| WO | WO-2014/044808 A2 | 3/2014 |
| WO | WO-2014/206500 A1 | 12/2014 |

OTHER PUBLICATIONS

No-Nonsense Cosmethic, "Sodium Hyaluronate Crosspolymer-2", Nov. 2011.*
Fritze et al. (Biochimica et Biophysica Acta 1758 (2006) 1633-1640).*
Agerup, B., et al., "NASHA(TM), The Monograph", Q-Med AB, 2008, 1-24 (28 pages).
International Preliminary Report on Patentability, Ch. I, for PCT/EP2017/084760 dated Jul. 2, 2019 (7 pages).
International Search Report for PCT/EP2017/084760 dated Dec. 2, 2018 (4 pages).
Wang et al., "In Vivo Stimulation of De Novo Collagen Production Caused by Cross-linked Hyaluronic Acid Dermal Filler Injections in Photodamaged Human Skin", Archives of Dermatology, American Medical Association, vol. 43, No. 2, Feb. 1, 2007, pp. 155-163 (9 pages).

* cited by examiner

*Primary Examiner* — Shaojia A Jiang
*Assistant Examiner* — Michael C Henry
(74) *Attorney, Agent, or Firm* — Foley & Lardner LLP; Sunit Talapatra (57) ABSTRACT

A micro- or nanoparticular vesicle comprises at least a crosslinked hyaluronic acid (HA), wherein the crosslinked hyaluronic acid is crosslinked by a chemical crosslinking agent, and wherein the degree of modification of said crosslinked hyaluronic acid with said chemical crosslinking agent is less than 1.9 mole %. Also disclosed are a method of manufacturing such vesicles, compositions comprising such vesicles and their uses.

17 Claims, 5 Drawing Sheets

Fig. 3

MICRO- OR NANOPARTICULAR VESICLES COMPRISING CROSSLINKED HYALURONIC ACID, COMPOSITIONS COMPRISING THE SAME AND METHOD FOR THEIR USE IN SKIN CARE

CROSS-REFERENCE TO RELATED APPLICATIONS

This application is a continuation of International Patent Application No. PCT/EP2017/084760 filed Dec. 28, 2017, published Jul. 5, 2018 as WO 2018/122343 A1, which claims priority to European Patent Application No. 16306846.3 filed Dec. 29, 2016. The contents of these applications are herein incorporated by reference in their entirety.

FIELD OF THE INVENTION

The present invention relates to micro- or nanoparticular vesicles comprising at least a hyaluronic acid (HA) crosslinked by a chemical crosslinking agent. The present invention also relates to a method of manufacturing the vesicles, compositions comprising such vesicles, and their cosmetic use in skin care, and notably against skin ageing.

BACKGROUND OF THE INVENTION

Ageing process occurs in every tissues in the human body, including skin, which is the most obvious indicator of age.

There are two distinct types of ageing. Ageing caused by the genes we inherit and depending on the passage of time is called chronological or intrinsic ageing. The other type of ageing is known as extrinsic ageing and is caused by environmental factors such as sun exposure (UV radiations), chemicals, microorganisms, food or environmental pollutants that can accelerate the ageing process. Age is not the determining factor in the condition of mature skin. Environmental factors that influence ageing of the skin play a central role. Tone, elasticity and epidermal regeneration capacity do not decline until advanced age in areas not exposed to light, whereas they do so prematurely in areas exposed to light. Young people who are exposed to a great amount of UV rays appear prematurely aged.

Intrinsic ageing, also known as the natural ageing process, is a continuous process that normally begins in the mid-twenties. Within the skin, collagen production slows down and elastin has a bit less spring. Dead skin cells do not shed as quickly and turnover of new skin cells may decrease slightly. While these changes usually begin in the twenties, the signs of intrinsic ageing are typically not visible for decades. The signs of intrinsic ageing are fine wrinkles, thin and transparent skin, loss of underlying fat, loss of density and firmness, which causes sagging skin, dry skin, and more dark spots.

With ageing, the loss of extracellular matrix and its major component hyaluronic acid (HA), which stabilizes the intracellular structures by forming viscoelastic network in which collagen and elastin fibers are embedded, induces loss of the skin mechanical functions. HA provides a cushion effect to the skin structures including the epidermis. Solidity of the skin is provided by the extracellular matrix and the loss of HA and consequently of the viscoelastic buffering system would contribute to easy tearing resulting in skin disruptions and skin dehydration leading to visible wrinkles on stratum corneum.

Viable epidermis and dermis are the essence of the skin. Structural destruction and loss of dermal collagen fiber bundles lead to wrinkling and increased appearance of muscular attachments. Irregular melanization leads to the apparition of lentigines, dark spots and melasma.

Most premature ageing is caused by sun exposure. Unlike chronological ageing, which depends on the passage of time, photoageing is directly correlated to the quantity of UV rays received during the course of lifetime. The effects of photodamage are often evident many years before intrinsic ageing is apparent. Individuals who have outdoor lifestyles, live in sunny climates and are lightly pigmented will experience the greatest degree of photoageing. All this factors influence extrinsic skin ageing process and can be distinguished from chronological ageing.

Ageing leads to a progressive decline in many biological functions in skin, eventually hindering cell division and growth. The biological signs of ageing involve both the epidermis and dermis layers characterized by decrease of epidermal thickness (that correlates with the reduced keratinocyte proliferation), reduction and disorganization of major key components, such as HA, collagens and other elastic fibers (proteoglycans and glycosaminoglycans), simultaneous increase in matrix metalloproteinases (MMP) production and flattening of the dermal-epidermal junction (DEJ). Collagens I and III, are the most abundant proteins in the dermis. They polymerize to form extended mechanically stiff fibrils, which confer tensile strength to the tissue. In addition to the fibrillar collagens, collagen VII is localized to perpendicularly oriented anchoring fibrils, which play a key role in securing the dermis to the DEJ. Skin ageing is associated to structural and compositional remodeling of dermal extracellular matrix and basement membrane proteins. Histologic changes in skin associated with ageing are a reduced epidermal thickness and a flattened DEJ.

With age, skin homeostasis is disrupted, metabolic activities are slowed, and endogenous production and accumulation of reactive oxygen species (ROS) leading to oxidative cellular stress and secretion of inflammatory mediators leading to more reactive and sensitive skin.

Many contributions have been published focusing on the role of HA during epidermal homeostasis, in fibroblast physiology and ageing, during tumorigenesis and tumor progression and reflecting the impact of HA in cosmetics or regenerative medicine.

More particularly, an important function of HA is to hold water in the intercellular matrix of the connective tissue. This water-binding capacity significantly contributes to the elasticity of the skin, serving as a water reservoir. With ageing and UV-B damage, the quantity and quality of HA in the skin decreases, which leads a loss of elasticity and the increase of wrinkles. HA is then a skin hydrating agent that can help restore water to dehydrated skin.

HA is naturally found in the human body.

In the epidermis, HA content is especially high in proliferating basal regions. Histological findings suggest that basal layer keratinocytes contain intracellular HA, whereas extracellular HA prevails in upper epidermal layers. Extracellular HA is thought to maintain diffusion and to open up spaces to facilitate cell migration.

The main source of HA in the dermis is fibroblasts with higher HA synthesis activity in the papillary dermis. The high flexibility of HA strands and their hydrophilicity enable these molecules to fill in any gaps within the extracellular matrix. The large hydrodynamic volume of HA is mainly explained by multiple hydrogen bonds between adjacent disaccharides but may also rely on the close interaction of HA with highly glycosylated proteoglycans. The resulting viscoelastic properties of HA in the dermis account for its support of tissue architecture and possibly function as a kind of 'hydraulic shock absorber' in the dermis.

Endogenous HA in skin exhibits a high cellular turnover rate and its amount is regulated and balanced by synthesis and degradation process. In dermis, HA has a half-life of less than one day and the turnover in epidermis is reported to be more rapid with a half time of two to three hours. Production of HA quantities as high as 12-60 pg/cell/24 h has been reported in dermal fibroblasts, whereas keratinocytes produce about 10-fold less. Moreover, cutaneous HA concentration varies at different anatomical sites, for example, forearm skin contains twice as much HA as back skin.

Synthesis of HA in the skin is accomplished by three HA synthases (HAS1, HAS2, HAS3) that incorporate uridine diphosphate (UDP) sugars into the non-reducing end of the growing sugar chains. They produce different sizes of polysaccharide chains. HAS2 is considered as the main HA synthase in fibroblasts while HAS2 and HAS3 show comparable degrees of activity in keratinocytes. HAS activity depends on post-translational modifications such as precise ubiquitination, phosphorylation or N-glycosylation. HA degradation is achieved either enzymatically by hyaluronidases (HYAL) or non-enzymatically by mechanisms such as free-radical-related depolymerization occurring in the presence of reactive oxygen species. HYAL1 and HYAL2 are considered to be the main active HYALs in tissues. In skin, HA catabolism/degradation is thought to differ in epidermis and dermis. Extracellular HA degradation is thought to be initiated through liberation from the ECM network by non-enzymatic mechanisms.

Human cells do not always produce HA efficiently lifelong. By age and following menopause, HA production declines in skin resulting in joint pain, mycofacial rigidity, loss of elasticity, ageing, dryness and development of wrinkles. Topically applied, HA can complement the deficiencies in endogenous HA and can contribute to reduce signs of skin ageing.

A large number of cosmetic products containing hyaluronic acid are available on the market such as for example, HA5™ (from SKIN MEDICA) cream or lotion which is a mix of five types of HA that smoothes the skin, thereby decreasing the appearance of fine lines and wrinkles. Also, more recently, combination products such as SKIN³™ have been developed.

SKIN³™ is a line of products featuring, based on a technology, registered under the tradename DERMATRIPLEX™, composed with more than twenty ingredients which integrates three particular technologies, notably:

a drug delivery system composed of seven bilayer membrane used to increase penetration of insoluble drugs and to incorporated water soluble) registered as NOVASOMES™, a gel consisting of hyaluronic acid long chains stabilized by natural and mobile interactions supported by a lower crosslinker rate (1.9-4.0%) registered under the tradename RHA resilient Hyaluronic Acid™, and a specific amino acid sequence of collagen, registered as TRUCOLLAGEN™.

Clinical studies have recently confirmed that topically applied HA on the skin reduces signs of skin ageing. HA, especially of high molecular weight, hydrate the skin by forming a film on the skin surface and preventing water loss. Whereas, low molecular weight of HA can penetrate skin to protect and support the epidermal hydration, to moisturize the Stratum Corneum continuously to assure high quality of the epidermal texture. Recent investigations about HA size and its effect on skin ageing have shown that low molecular weight HA of approximately 50 kDa, has revealed significantly higher skin penetration rates than larger sized HA («Human skin penetration of hyaluronic acid of different molecular weights as probed by Raman spectroscopy», Essendoubi M et al.; Skin Res Technol; 2015; 0: 1-8). Indeed, low molecular weight HA can influence the expression of many genes including those contributing to keratinocyte differentiation and formation of intercellular tight junction complexes (ZO-1, claudin-1 makers) which are reported to be reduced in aged and photodamaged skin, thereby improving the skin quality. However, the benefits of topical applied HA are limited by its molecular size interfering with efficient skin penetration for better effect.

Considering the above, there is a need to develop improved cosmetic compositions notably for use in skin care, that are stable, easy and fast to apply, which are simple to use, which do not require excessive applications and which present a long-lasting effect.

SUMMARY OF THE INVENTION

A first object of the solution proposed by the invention to remedy this problem is to provide a micro- or nanoparticular vesicle comprising at least a crosslinked hyaluronic acid (HA), wherein the crosslinked hyaluronic acid is crosslinked by a chemical crosslinking agent, and wherein the degree of modification of said crosslinked hyaluronic acid with said chemical crosslinking agent is less than 1.9 mole %.

A second object proposed by the invention is a method of manufacturing a vesicle according to the invention, comprising the steps of:

preparing a phase containing the non-ionic surfactants, preparing an aqueous phase containing a crosslinked HA, wherein the crosslinked hyaluronic acid is crosslinked by a chemical crosslinking agent, and wherein the degree of modification of said crosslinked hyaluronic acid with said chemical crosslinking agent is less than 1.9 mole %, mixing said aqueous phase into said non-ionic surfactant phase with a controlled stirring and heating mode, allowing the formation of the multilamellar vesicles composed of surfactant bi-layers, and diluting the preparation containing said vesicles with water.

A third object proposed by the invention is a composition comprising, in a physiologically acceptable medium, a micro- or nanoparticular vesicle as disclose herein.

A fourth object proposed by the invention is the cosmetic use of the vesicle or the composition as disclosed herein, in skin care and/or anti-ageing treatment.

These and other features, aspects and advantages of the invention will become better understood with reference to the following description and drawings.

BRIEF DESCRIPTION OF THE DRAWINGS

The invention will now be described in more details, by way of example only, with reference to the accompanying drawings in which:

FIGS. 2a, 2b, 2c, 2d, 2e and 2f show the results of a Raman Spectroscopy:

FIG. 3 shows thickness measures of the Stratum Corneum in the following conditions:

two measures for untreated skin used as negative control (T0h/T8h)
one measure for NASHA™ (T8h)
one measure for NASHA™ loaded into and/or onto SPHERULITES™ (T8h)
one measure for PRIMALHYAL 50™ (T8h).

DETAILED DESCRIPTION OF THE INVENTION

Surprisingly, the Applicant has revealed that it was possible to develop an improved stable cosmetic composition comprising a specific category of crosslinked hyaluronic acid having a degree of modification less than 1.9 mole %, and micro- or nanoparticular vesicles, the crosslinked HA being preferably introduced into and/or onto the micro- or nanoparticular vesicles. The resulting combination has shown notably high biocompatibility and long duration. Moreover, depending on the crosslinked hyaluronic acid used, the resulting gel shows a high gel strength.

Micro- or Nanoparticular Vesicles

As indicated above, the vesicles according to the invention are micro- or nanoparticular vesicles comprising at least a crosslinked hyaluronic acid (HA).

Among the micro- or nanoparticular vesicles, it is possible to use all carrier systems enabling controlled release of the HA according to the invention, such as microcapsules, microspheres, macromolecular complexes, nanospheres, nanocapsules or latex.

As non-limiting examples of micro- or nanoparticular vesicles, it is possible to cite the multilamellar vesicles NOVASOMES™, the multilamellar vesicles called SPHERULITES™, microcapsules based on polyurethane, polyurea resin, polyamide resin, polyamide-polyurea resin, polycarbonate resin, polysulphonate resin and polysulphonamide resin.

In a particular embodiment, vesicles are modified forms of liposomes or a variation of niosomes prepared from the mixture of monoester of polyoxyethylene fatty acids, cholesterol and free fatty acids at 74/22/4 ratio. They are also defined as non-phospholipid paucilamellar vesicles.

Preferably, vesicles consist of two to seven bilayered shells that surround an unstructured space occupied by a large amorphous core of hydrophilic or hydrophobic materials. These molecules have a hydrophilic head group attached to a hydrophobic tail and include long-chain fatty alcohols and derivatives, long-chain acids, long-chain amino and glycerolipids.

NOVASOMES™ are a preferred example of such vesicles.

In another particular embodiment, the vesicles are micro- or nanoparticular multilamellar vesicles constituted of concentric membranes comprising at least one non-ionic surfactant of the sucrose ester type comprising at least one chain arising from a linear or branched, saturated or unsaturated, optionally mono- or polyhydroxylated C12 to C22 fatty acid.

Preferably, the vesicles are multilamellar microvesicles, with an internal structure of concentric spherical bilayers made of water and amphiphile, created by the controlled shearing of liquid-crystalline phases. Application WO 97/00623 notably discloses carriers suitable for such vesicles, containing non-ionic surfactants forming onion-structured microcapsules within which an active material is encapsulated. Application WO 97/00623 also discloses compositions suitable for use as cosmetics containing at least one active material encapsulated in said microcapsules. U.S. Pat. No. 5,792,472 discloses a process of preparation of such vesicles with controlled size.

SPHERULITES™ are a preferred example of such vesicles.

In a further particular embodiment, the vesicles are multilamellar vesicles that encapsulate active ingredients. Particularly, they can be composed of surfactant bi-layers and aqueous interfaces. More particularly, they have a concentric structure.

In a further particular embodiment, the vesicles can comprise between 3 to 3000 surfactant bi-layers, preferably between 10 to 1000 surfactant bi-layers. Particularly, the vesicles can be hydrodispersible or lipodispersible. More particularly, the vesicles can encapsulate lipophilic and/or hydrophilic compounds, such as active agents.

In a preferred embodiment, the encapsulation rate of lipophilic compounds is less than 20%. In a further preferred embodiment, the encapsulation rate of hydrophilic compounds is of 40% or less.

In a further particular embodiment, the vesicles as disclosed herein further comprise sucrose palmitate or sucrose tristearate with at least:

Tocopherol, Tocopheryl acetate or butylene glycol;
Glyceryl linoleate or sodium benzoate;
Benzyl alcohol or phenoxyethanol; and eventually
Potassium sorbate, prunus Amygdalus Dulcis Oil or Citric Acid.

More preferably, the vesicles as disclosed herein comprise at least:

Sucrose palmitate;
Tocopheryl acetate;
Glyceryl linoleate; and
Phenoxyethanol.

Even more preferably, the vesicles as disclosed herein comprise:

Water;
Sucrose palmitate;
Tocopheryl acetate;
Glyceryl linoleate;
Phenoxyethanol;
Potassium sorbate; and
Citric acid.

In a further particular embodiment, the vesicles as disclosed herein can be either charged or non-charged. When these vesicles are charged, they are advantageously cationic. For example, the vesicles can be positively charged by addition of a cationic polymer such as Guarhydroxypropyltrimonium chloride or a chitosan derivative such as chitosanide.

In a specific embodiment, the vesicles as disclosed herein are combined with an encapsulated material loaded into or onto said vesicles. Preferably, the encapsulated material is cross linked hyaluronic acid (HA).

When vesicles are positively charged, the vesicles bind to skin and hair. They ensure a regular and controlled release of the encapsulated material at the surface of skin and on hair. Thus, even after a mechanical action, for example cleaning, the benefits of the composition according to the invention are preserved. This progressive release effect makes it possible to maintain the action of HA over time. The cationic vesicles optimize the activity on the skin surface by fixing themselves on the upper layers of the skin.

When the vesicles are not charged, they are called non-ionic. In this case, in addition to the aforementioned prolonged release effect, their presence promotes the diffusion of encapsulated material through skin. Thus, the non-ionic vesicles bring the compounds into the deep layers of the skin by diffusing through epidermal layers and into the dermis.

In a particular embodiment, cosmetic compositions as disclosed herein comprise both cationic micro- or nanoparticular vesicles and non-ionic micro- or nanoparticular vesicles. In this case, the benefit lies in the respective contribution of each type of vesicles.

In a further particular embodiment, the micro- or nanoparticular vesicles comprising at least a crosslinked HA as disclosed herein have a diameter between 0.01 μm and 150 μm. If these vesicles are nanoparticular vesicles, their diameter is preferably between 0.1 μm and 0.5 μm and, if they are microparticular vesicles, their diameter is preferably between 1 μm and 50 μm.

Preferably, the micro- or nanoparticular vesicles diameter is between 0.1 μm and 20 μm, preferably between 0.1 μm and 5 μm, more preferably between 0.8 and 2 μm, more preferably 1 μm.

The compounds that are encapsulated by the micro- or nanoparticular vesicles as disclosed herein are progressively released. The kinetics and thermodynamics of the release of the encapsulated compounds can be monitored. It has been shown that vesicles of the invention can release compounds during 48 hours after application.

It has also been shown that the stability of the encapsulation technology is high. The vesicles of the invention show good tolerance to salt and a good stability from pH 3 to pH 9. The vesicles as disclosed herein are thermosensitive and can be damaged at a temperature of more than 50° C.

In a further particular embodiment, vesicles can be incorporated at the end of the formulation at a temperature of less than 45° C. The vesicles can also be predispersed in water (50/50) under stirring if necessary. For low viscosity compositions such as for a shampoo for example, it is recommended to add a thickener in order to avoid sedimentation of the vesicles.

Crosslinking Hyaluronic Acid (HA)

According to the present invention, the micro- or nanoparticular vesicles further comprise at least a crosslinked HA having a degree of modification of less than 1.9 mole %.

Hyaluronic acid or hyaluronan is a natural carbohydrate linear polysaccharide found in almost all living organisms. Its chemical structure is consisting of alternating repeating disaccharide units composed of D-glucuronic acid and N-acetylglucosamine linked together through alternating beta-1,4 and beta-1,3 glycosidic bonds. The number of repetitions can reach up to 10,000 with approximately from $10^2$ to $10^4$ kDa molecular weight.

Generally, the term "hyaluronic acid" can also encompass all variants and combinations of variants of hyaluronic acid, hyaluronate or hyaluronan, of various chain lengths and charge states, as well as with various chemical modifications, including cross-linking. That is, the term also encompasses the various hyaluronate salts of hyaluronic acid with various counter ions, such as sodium hyaluronate. Various modifications of the hyaluronic acid are also encompassed by the term, such as oxidation, e.g. oxidation of —$CH_2OH$ groups to —CHO and/or —COOH; periodate oxidation of vicinal hydroxyl groups, optionally followed by reduction, e.g. reduction of —CHO to —$CH_2OH$ or coupling with amines to form imines followed by reduction to secondary amines; sulphation; deamidation, optionally followed by deamination or amide formation with new acids; esterification; crosslinking; substitutions with various compounds, e.g. using a crosslinking agent or a carbodiimide assisted coupling; including coupling of different molecules, such as proteins, peptides and active drug components, to hyaluronic acid; and deacetylation. Other examples of modifications are isourea, hydrazide, bromocyan, monoepoxide and monosulfone couplings.

HA is a highly hydrophilic macromolecule which plays a key role in the transport of water in skin maintaining the hydration and stabilizing the structure of epidermis and dermis. HA plays an important role in the structural characteristics of many tissues. Due to its unique coil structure in aqueous solutions, HA exhibits a highly effective moisturizing property since it can retain till 1000 times its weight in water what makes HA so important for maintaining tissue structure and volume. Its remarkable water holding property and its unique viscoelastic and physicochemical properties, coupled with its lack of immunogenicity or toxicity, has led to the development of numerous HA-based medical devices and cosmetic and dermo cosmetic products including skin moisturizers, osteoarthritis treatment, ophthalmic surgery, adhesion prevention after abdominal surgery, and wound healing.

Crosslinked HA are often characterized in terms of "degree of modification" "crosslinking ratio", and "degree of crosslinking" (Keene et al., Carbohydrate Polymers, 2013, 91, 410-418).

The degree of modification (mole %) describes the amount of crosslinking agent(s) that is bound to HA, i.e. molar amount of bound cross-linking agent(s) relative to the total molar amount of repeating HA disaccharide units. The degree of modification reflects to what degree the HA has been chemically modified by the crosslinking agent. Traditional crosslinking relates to extensive modification, with high degree of synthetic (chemical) crosslinks up to 40% (40 crosslinker molecules per 100 HA-disaccharides). In a preferred embodiment, the degree of modification of crosslinked HA with a chemical crosslinking agent is less than 15 mole %, preferably less than 1.9%, more preferably between 0.1 and 1.9 mole %.

Crosslinked HA may also be characterized by the cross-linker ratio or crosslinking ratio (CrR). The cross-linker ratio (CrR) describes the proportion of total bound cross-linking agent (HA-X-HA and HA-X) that has bound two (or more) disaccharides (only HA-X-HA). The cross-linker ratio (CrR) of HA generally ranges between 0.01 and 0.50. In a preferred embodiment, the CrR is less than 0.30, preferably between 0.10 and 0.20, more preferably 0.10 or 0.20.

Crosslinked HA may also be characterized by the degree of crosslinking (CrD) corresponding to the stoichiometric ratio between the cross-linking agent that are double-linked and HA disaccharide units. In a preferred embodiment, the CrD is between 0.2 and 0.8, preferably between 0.2 and 0.5, more preferably between 0.2 and 0.4, even more preferably 0.2.

Reaction conditions for crosslinking and suitable analytical techniques for determining the degree of modification are all well known to the person skilled in the art, who easily can adjust these and other relevant factors and thereby provide suitable conditions to obtain such a degree of modification and verify the resulting product characteristics with respect to the degree of modification.

Preferably, the degree of modification of said crosslinked HA with said chemical crosslinking agent being in the range of 0.1 to less than 1.9 mole %.

This results in obtaining an improved stabilized crosslinked HA with minimal modification, low degree of synthetic crosslinks and high degree of natural crosslinks (entanglements) which confers an optimized long-term effect of HA.

Crosslinking of the HA as disclosed herein is achieved by modification with a chemical crosslinking agent.

The chemical crosslinking agent may for example be selected from the group consisting of divinyl sulfone, multiepoxides and diepoxides. According to an embodiment, the HA is crosslinked by a bi- or polyfunctional crosslinking agent comprising two or more glycidyl ether functional groups. According to a preferred embodiment, the chemical crosslinking agent is selected from the group consisting of 1,4-butanediol diglycidyl ether (BDDE), 1,2-ethanediol diglycidyl ether (EDDE) and diepoxyoctane. According to a more preferred embodiment, the chemical crosslinking agent is 1,4-butanediol diglycidyl ether (BDDE).

The crosslinked HA as disclosed herein may be a gel, or a hydrogel. That is, it can be regarded as a water-insoluble, but substantially dilute crosslinked system of HA molecules when subjected to a liquid, typically an aqueous liquid.

The gel contains mostly liquid and can e.g. contain 90-99.9% water by weight, but it behaves like a solid due to a three-dimensional crosslinked HA network within the liquid. Due to its significant liquid content, the gel is structurally flexible and similar to a natural tissue.

Such a crosslinked HA according to the invention confers high gel strength, long duration and high biocompatibility.

The crosslinked HA as disclosed herein is then biocompatible. This implies that no, or only very mild, immune response occurs in the treated individual. That is, no or only very mild undesirable local or systemic effects occur in the treated individual.

As mentioned, crosslinking of HA to form the crosslinked HA gel may for example be achieved by modification with a chemical crosslinking agent, for example BDDE (1,4-butanediol diglycidylether). The HA concentration and the extent of crosslinking affect the mechanical properties, e.g. the elastic modulus G', and stability properties of the gel.

A BDDE (1,4-butanediol diglycidylether) crosslinked HA gel may for example be prepared according to the method described in Examples 1 and 2 of published international patent application WO 97/04012.

In a preferred embodiment, the HA of the vesicle of the invention is at least present in the form of a sodium hyaluronate crosspolymer-2 (also called NASHA™ (Non-Animal Stabilized Hyaluronic Acid)), which is a crosslinked HA gel crosslinked by a chemical crosslinking agent, which is preferably 1,4-butanediol diglycidyl ether (BDDE), wherein the concentration of said HA is in the range of 10 to 30 mg/ml and the degree of modification with said chemical crosslinking agent is less than 1.9 mole %, more preferably about 1.0 mole %.

In such preferred embodiment, sodium hyaluronate crosspolymer-2 significantly increases HA absorption up to 90 μm into the skin layers and protects HA against biodegradation.

The vesicle as disclosed herein may also comprise a portion of HA which is not crosslinked ("Non crosslinked" HA), i.e. not bound to the three-dimensional crosslinked HA network. However, it is preferred that at least 50% by weight, preferably at least 60% by weight, more preferably at least 70% by weight, and most preferably at least 80% by weight, of the HA in a gel composition form part of the crosslinked HA network.

According to this particular embodiment wherein the vesicle also comprises a portion of not crosslinked HA, the vesicle improves both immediate and long-lasting hydration of the skin.

It has been shown that, depending on the type of crosslinked HA used and/or depending on the concentration of said crosslinked HA, the vesicle as disclosed herein contains the crosslinked HA into and/or onto the micro- or nanoparticular vesicles. The crosslinked HA is loaded into and/or onto the micro- or nanoparticular vesicles. More preferably, the crosslinked HA is loaded onto the vesicles.

The term "into" encompasses the inside and the lower layers of the micro- or nanoparticular vesicles. The lower layers of the micro- or nanoparticular vesicles refer to the 30% of the layers that can be found between the center and the surface of the micro- or nanoparticular vesicles. More preferably, the term "into" refers only to the inside of the micro- or nanoparticular vesicles.

The term "onto" encompasses the surface and the upper layers of the micro- or nanoparticular vesicles. The upper layers of the micro- or nanoparticular vesicles refer to the 70% of the layers that can be found between the surface and the center of the micro- or nanoparticular vesicles. More preferably, the term "onto" refers only to the surface and to the 50% of the layers that can be found between the surface and the center of the micro- or nanoparticular vesicles.

The crosslinked HA according to the invention is preferably loaded into or onto the micro- or nanoparticular vesicles at a concentration of between 0.01% and 5% (w/w). More preferably the crosslinked HA is loaded into and/or onto the vesicles at a concentration of between 0.1% and 0.5% (w/w). Even more preferably, the crosslinked HA is loaded into or onto the micro- or nanoparticular vesicles at a concentration of 0.175%, 0.35% or 0.5% (w/w).

In a particular embodiment, the crosslinked HA is loaded into the micro- or nanoparticular vesicles as disclosed herein.

In another particular embodiment, the crosslinked HA is loaded onto the micro- or nanoparticular vesicles as disclosed herein.

It has been shown that, when the crosslinked HA is acid is sodium hyaluronate crosspolymer-2 (e.g. available under the trademark NASHA™), it is generally adsorbed onto the vesicles.

It has been shown that the advantages of using of sodium hyaluronate crosspolymer-2 loaded preferably on vesicles versus sodium hyaluronate crosspolymer-2 powder, is to have an improved skin penetration profile and to promote long lasting deeper hydration effect once applied onto the skin. Moreover, as compared to other encapsulated hyaluronic acids, the loading is twice higher. Finally, it has been shown that the use of sodium hyaluronate crosspolymer-2 as a crosslinked HA boosts hydration onto the skin maintaining the skin barrier integrity.

Method of Manufacture

Another object of the invention is a method of manufacturing a micro- or nanoparticular multilamellar vesicle as disclosed herein, comprising the steps of:
  preparing a phase containing the non-ionic surfactants,
  preparing an aqueous phase containing a crosslinked HA, wherein the crosslinked hyaluronic acid is crosslinked by a chemical crosslinking agent, and wherein the degree of modification of said crosslinked hyaluronic acid with said chemical crosslinking agent is less than 1.9 mole %, mixing said aqueous phase into said non-ionic surfactant phase with a controlled stirring and heating mode, allowing the formation of the multilamellar vesicles composed of surfactant bi-layers, and diluting the preparation containing said vesicles with water. In a particular embodiment, the crosslinked HA is loaded into the micro- or nanoparticular vesicles.

In another particular embodiment, the crosslinked HA is loaded onto the micro- or nanoparticular vesicles.

Composition

Another object of the invention is a composition comprising, in a physiologically acceptable medium, a micro- or nanoparticular vesicle as disclosed herein.

For instance, the physiologically acceptable medium may include a number of optional excipients at levels necessary to achieve desirable compositional aesthetics, fragrance presentation, or skin feel and conditioning benefits to the skin.

The following is a non-limiting disclosure of typical optional ingredients to be used together with the claimed invention:

abrasive agent, absorbent agent, anticaking agent, antidandruff agent, antifoaming agent, antimicrobial agent, antioxidant agent, antistatic agent, astringent agent, binding agent, bleaching agent, buffering agent, bulking agent, chelating agent, cleansing agent, cosmetic colorant agent, denaturant agent, deodorant, emollient, emulsifying agent, emulsion agent, emulsion stabilizing agent, film-forming agent, flavouring agent, foam boosting agent, gel forming agent, hair conditioning agent, hair fixing agent, humectant, masking agent, moisturizing agent, nail conditioning agent, opacifying agent, oral care agent, perfuming agent, plasticizer, preservative, refatting agent, refreshing agent, skin conditioning agent, skin protecting agent, smoothing agent, solvent, surfactant, tonic agent, UV-absorber, UV-filter and viscosity controlling agent.

In a particular embodiment, the compositions are formulated for topical and/or parenteral application.

The compositions may be in any of the galenical forms normally employed for topical administration. Exemplary topical preparations include preparations in liquid, pasty or solid form, and more particularly in the form of ointments, aqueous, aqueous-alcoholic or oily solutions, dispersions of the optionally two-phase lotion type, serum, aqueous, anhydrous or lipophilic gels, powders, impregnated pads, syndets, wipes, sprays, foams, sticks, shampoos, compresses, washing bases, emulsions of liquid or semi-liquid consistency of the milk type, obtained by dispersion of a fatty phase in an aqueous phase (O/W) or vice versa (W/O), a microemulsion, suspensions or emulsions of soft, semi-liquid or solid consistency of the white or colored cream, gel or ointment type.

When they are for parenteral administration, the compositions may be administered subcutaneously or intradermally. Exemplary parenteral compositions include compositions in the form of solutions or suspensions for perfusion or for injection.

The concentration of the vesicle of the invention is preferably between 0.1% and 10% by weight relative to the total weight of the composition. More preferably, the concentration is between 0.5% and 5% by weight relative to the total weight of the composition. Even more preferably, the concentration is about 1%, about 2% or about 3% by weight relative to the total weight of the composition.

Application

Another object of the invention is a cosmetic use of a composition as disclosed herein in skin care and/or anti-ageing treatment, notably for:

decreasing and/or preventing the characteristics of wrinkles, small wrinkles and/or fine lines of the skin;

improving and/or decreasing the microrelief of the skin;

smoothing the skin;

plumping the skin;

improving the density of the skin;

maintaining and/or restoring skin elasticity;

maintaining and/or restoring skin barrier integrity; maintaining and/or restoring skin firmness; and/or maintaining and/or restoring the cohesion of skin compartments, in particular the cohesion of the derm within the skin.

EXAMPLES

Example 1

Study of the Epidermis Distribution of the Vesicle According to the Invention

1a. Skin penetration of PRIMALHYAL 50™, NASHA™ and NASHA™ loaded into and/or onto SPHERULITES™ vesicles:

The present example compares the penetration into the skin of:

linear HA with low molecular weight (Non crosslinked HA), crosslinked HA of high molecular weight, and a vesicle according to the invention.

More particularly, the three following products are tested:
1. PRIMALHYAL 50™ in aqueous solution 0.35% w/w, i.e. a low molecular weight hyaluronic acid grade (MW: 20-50 KDA)
2. NASHA™, i.e. crosslinked HA, in aqueous solution 0.35% w/w
3. crosslinked HA NASHA™ combined with SPHERULITES™ vesicles (SPHERULITES™ vesicles loaded with 0.35% w/w NASHA™).

For this Study, five cutaneous abdominal human skin explants (full thickness dermatomed skin) from one donor were used:

two for untreated skin used as negative control (T0h/T8h)

one for NASHA™ (T8h)

one for NASHA™ loaded into and/or onto SPHERULITES™ vesicles (T8h)

one for PRIMALHYAL 50™ (T8h).

5 mg/cm$^2$ of each product were applied onto the explants and then incubated at 32° C. for 8 hours.

After 8 hours, explants were cleaned prior to analysis.

The analysis performed are:

HA derivatives Raman spectra analysis; and

Stratum Corneum thickness measure.

1 b. Raman Spectroscopy:

Raman spectroscopy is a spectroscopic technique used to observe vibrational, rotational, and other low-frequency modes in a system. Raman spectroscopy is commonly used in chemistry to provide a fingerprint by which compounds can be identified.

Figure 1:
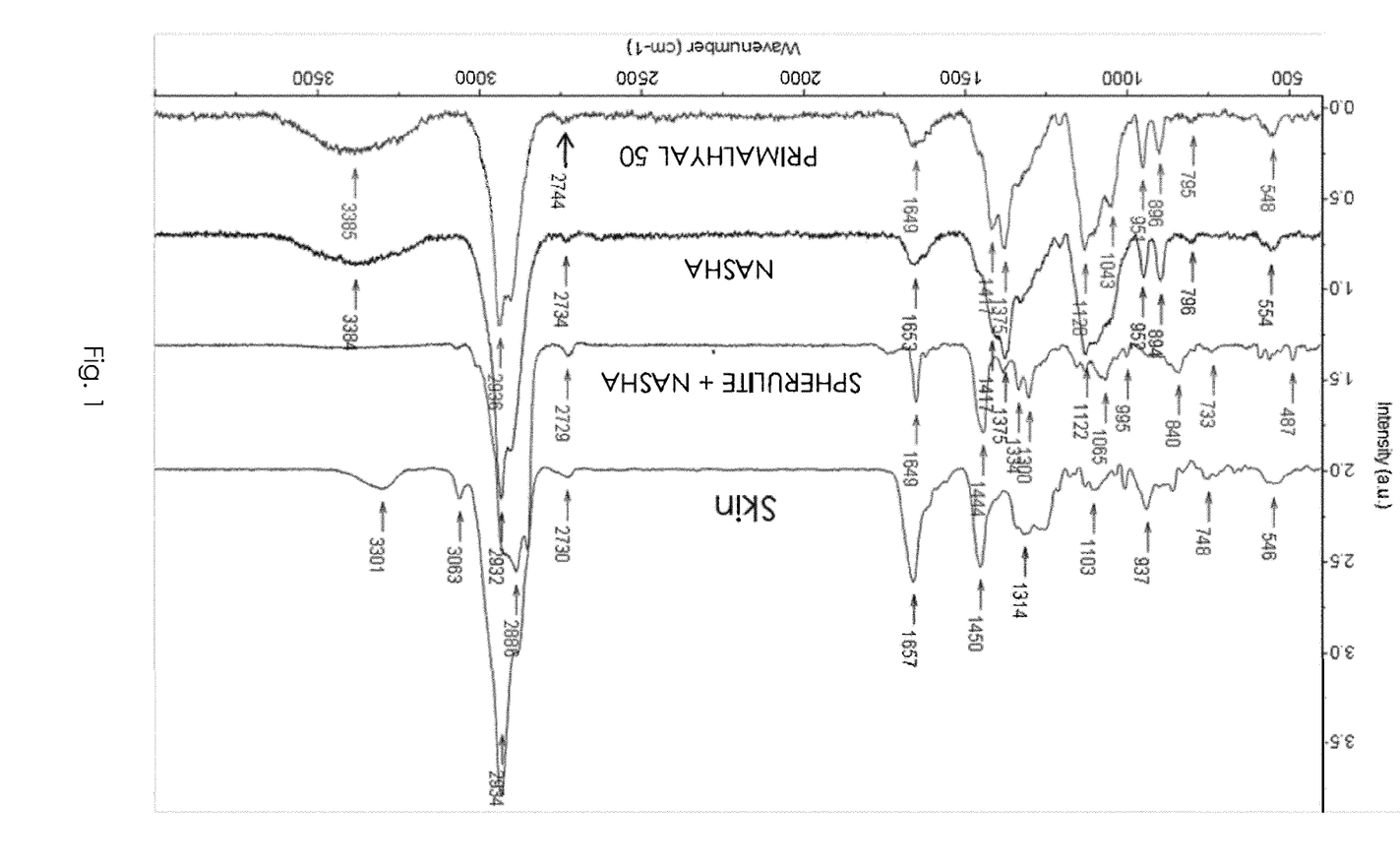
FIG. 1 shows the reference Raman spectrum of the skin and each tested product at 0.35% w/w (HA derivatives)

FIG. 1 shows the reference Raman spectrum of the skin and each product at 0.35% w/w (HA derivatives).

For the Raman Fitting Analysis, Raman spectral acquisition were recorded from three cryo-skin sections per explant on the 400 to 4000 cm-1 in a zone of X:100 up to 120 μm/Y:10 μm with 5 μm step (excitation source 600 nm laser):

72 spectra per Raman picture/9 Raman pictures

The results of this Raman Spectroscopy are illustrated at FIGS. 2a, 2b, 2c, 2d, 2e and 2f.

Figure 2A:
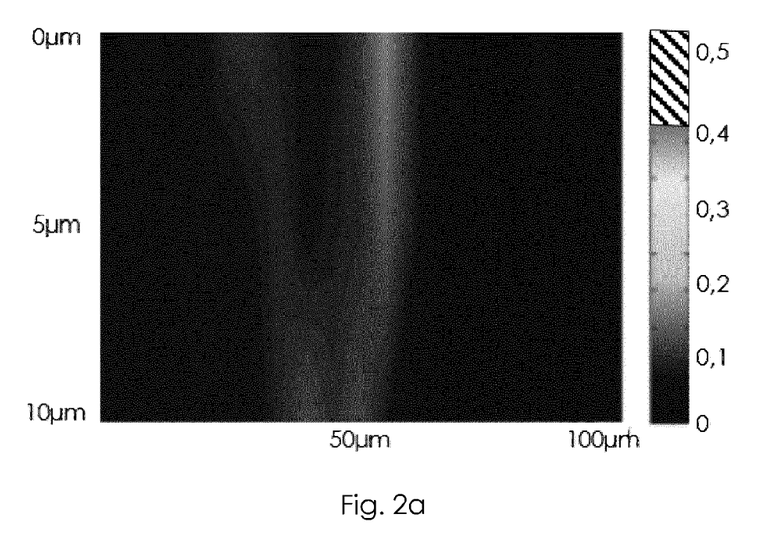
FIGS. 2a and 2b show the Epidermis distribution of PRIMALHYAL 50™.
Figure 2B:
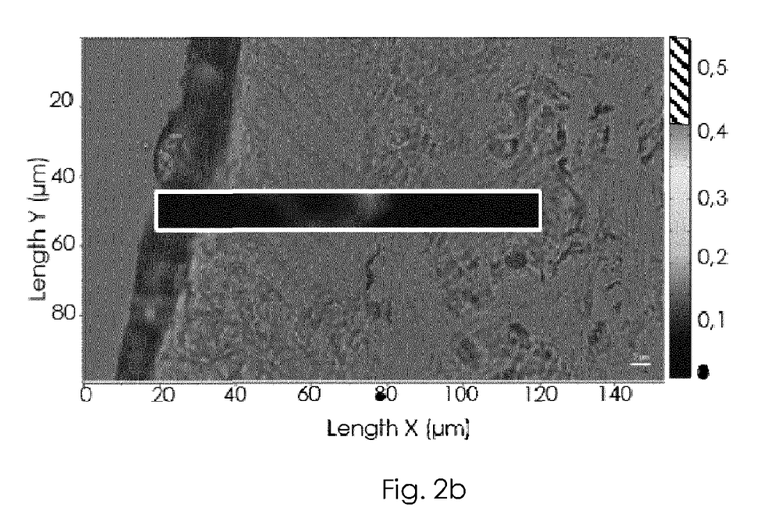

FIGS. 2a and 2b show the Epidermis distribution of PRIMALHYAL 50™. It appears that PRIMALHYAL 50™ was not detected under the operational conditions.

Figure 2C:
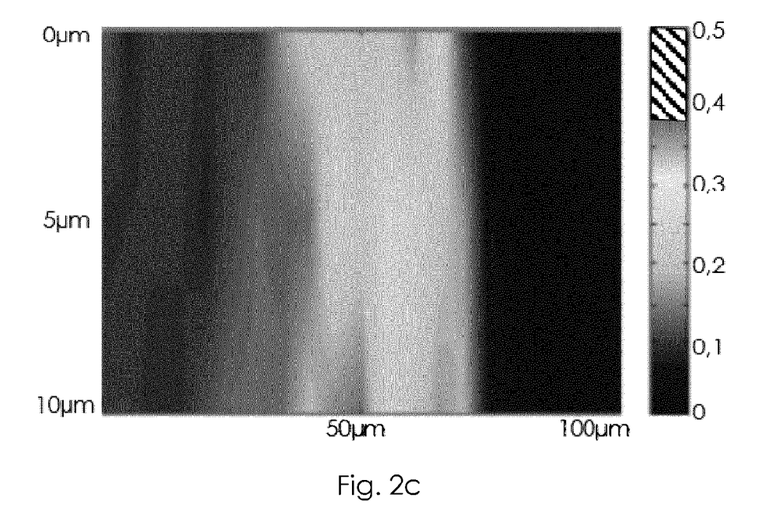
FIGS. 2c and 2d show the Epidermis distribution of NASHA™.
Figure 2D:
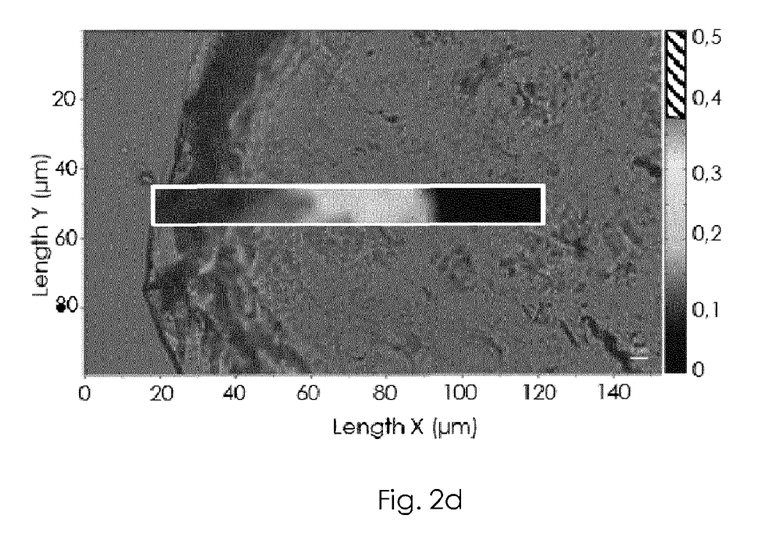

FIGS. 2c and 2d show the Epidermis distribution of NASHA™. Skin penetration up to 70 μm could be observed without gradient of diffusion.

Figure 2E:
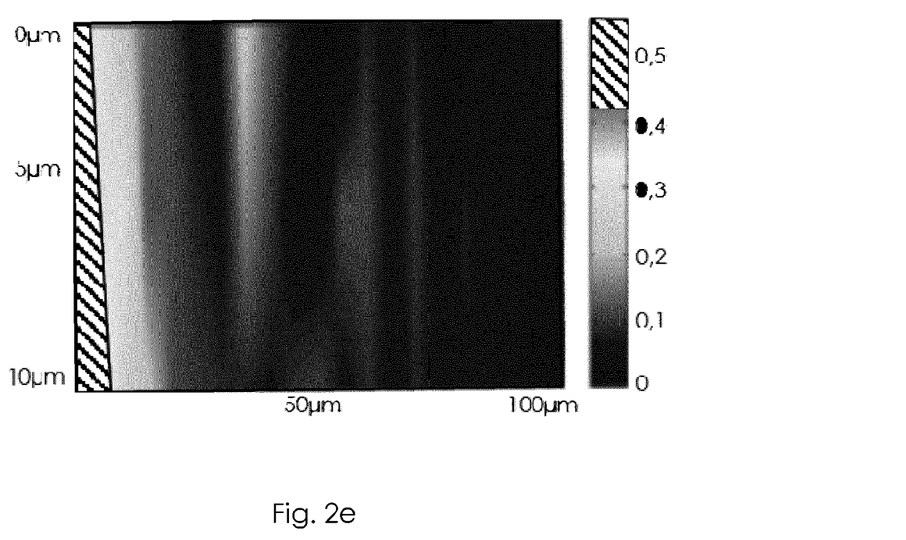
FIGS. 2e and 2f show the Epidermis distribution of vesicles according to the invention, i.e. NASHA™ loaded into and/or onto SPHERULITES™.
Figure 2F:
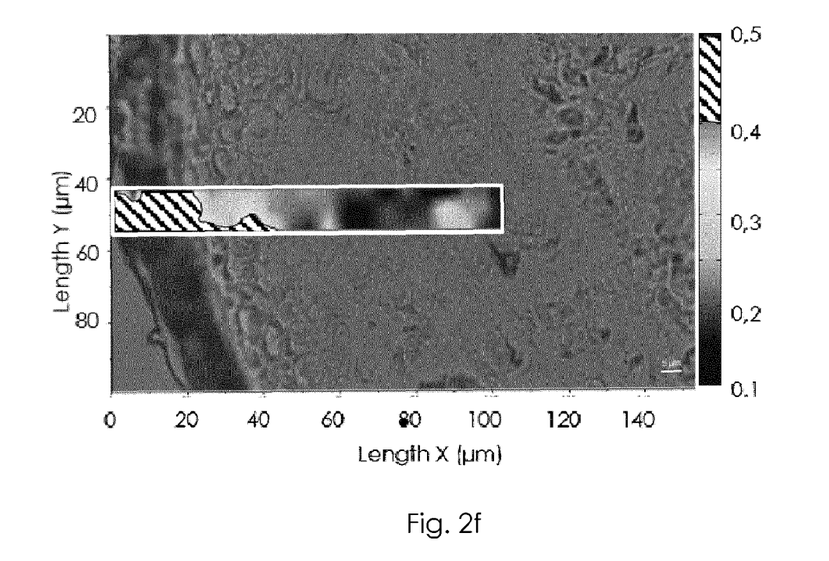

FIGS. 2e and 2f show the Epidermis distribution of NASHA™ loaded into and/or onto SPHERULITES™ vesicles. Skin penetration up to 90 μm with a gradient of diffusion in the epidermis could be observed. Thus, a higher concentration of the tested vesicle according to the invention could be observed in the stratum corneum, in comparison with the two other products tested (PRIMALHYAL 50™ and NASHA™).

This Raman Spectroscopy Study demonstrates the penetration into the skin of linear and crosslinked HA derivatives, and demonstrate that SPHERULITES™ vesicles as NASHA™ carrier promote the NASHA™ penetration into the deeper layers of the skin.

1c. Stratum Corneum (SC) thickness

The thickness measures of the Stratum Corneum in the following conditions were performed:
  two measures for untreated skin used as negative control (T0h/T8h)
  one measure for NASHA™ (T8h)
  one measure for NASHA™ loaded into and/or onto SPHERULITES™ vesicles (T8h)
  one measure for PRIMALHYAL 50™ used as positive control (T8h).

Figure 3:
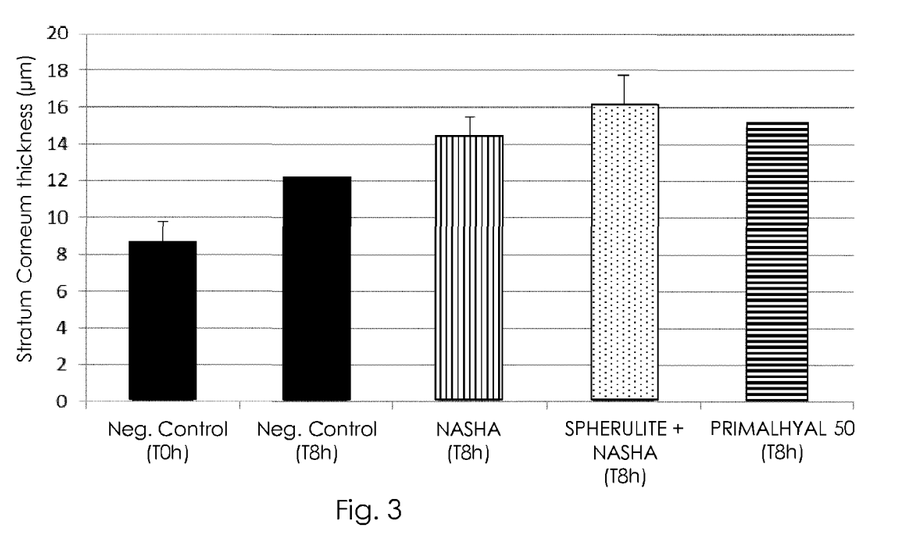

The results are illustrated at FIG. 3.

As can be shown at FIG. 3, the thickness of the Stratum Corneum for untreated skin is between 8 μm and 12 μm, the thickness of the Stratum Corneum for Primalhyal 50 or for NASHA™ is approximatively of 14.5 μm to 15 μm. Surprisingly, the thickness of the Stratum Corneum for NASHA™ loaded into and/or onto SPHERULITES™ vesicles was found to be 16 μm thick, i.e. between 33% and 100% thicker than for the untreated skin. This higher Stratum Corneum thickness with encapsulated NASHA™ (NASHA™ loaded into and/or onto SPHERULITES™) suggests a «reservoir effect».

Conclusion:

The present Study showed that NASHA™ penetrates the skin and that SPHERULITES™ vesicles are improved NASHA™ carriers, that foster the penetration of NASHA™ into the epidermis. SPHERULITES™ vesicles increase NASHA™ amount in the upper layers of the skin, thus building a «reservoir effect» which will gradually release NASHA™ over time into the deeper layers of the skin.

Thus, the product combining NASHA™ with SPHERULITES™ vesicles showed unexpected advantages versus NASHA™ powder.

The vesicle according to the invention:
results in an improved skin penetration profile;
promotes long lasting deeper hydration effect once applied onto the skin.

Moreover, as compared to other encapsulated HAs, it appears that the loading is twice higher and in addition, NASHA™ as a crosslinked-HA boosts hydration onto the skin by maintaining the skin barrier integrity.

Example 2

Stability Results of Cosmetic Compositions Comprising the Vesicle According to the Invention This example shows the stability of compositions comprising the vesicle according to the invention. More particularly, the vesicle according to the invention in this example, combines SPHERULITES™ vesicles loaded wish NASHA™, respectively at a concentration of 0.175% w/w, 0.35% w/w and 0.5% w/w. The SPHERULITES™ vesicles or multilamellar vesicles of onion structure were prepared according to applications WO 93/19735 and WO 95/18601

At every dosage, Maltese crosses show the presence of SPHERULITES™ vesicles. Maltese cross is a set of four symmetrically disposed sectors of high extinction that is displayed when a polymer is observed under polarized lights. This is usually observed when trying to observe SPHERULITES™ vesicles in the composition.

The stability Study is carried out during 12 months at 4° C., 20° C. and 45° C.

2a. Stability of SPHERULITES™ vesicles loaded wish 0.175% w/w NASHA™

TABLE 1

| (0.175% w/w at 4° C.): | | | | | |
|---|---|---|---|---|---|
| | T0 month | T1 month | T2 months | T3 months | T6 months |
| General Aspect | Cream | Cream + slight sedimentation | Cream + slight sedimentation | Cream + slight sedimentation | Cream + slight sedimentation |
| Color | White | White | White | White | White |
| pH | 5.55 | 5.48 | 5.57 | 5.55 | 5.48 |
| Dry Matter 105° C. | 32.00% | 32.58% | 32.22% | 32.15% | 30.74% |
| Total Mesophiles Germs | <11 | <10 | <10 | <10 | Accurate (<10) |
| Yeast and molds | <11 | <10 | <10 | <10 | Accurate (<10) |
| Particle Size (lazer granulometry) | 0.946 μm | — | — | 1.199 μm | 0.851 μm |
| Storage Temperature | | | 4° C. | | |

TABLE 2

(0.175% w/w at 20° C.):

| | T0 month | T1 month | T2 months | T3 months |
|---|---|---|---|---|
| General Aspect | Cream | Cream + slight sedimentation | Cream + slight sedimentation | Cream + slight sedimentation |
| Color | White | White | White | White |
| pH | 5.55 | 5.54 | 5.58 | 5.55 |
| Dry Matter 105° C. | 32.00% | 27.97% | 32.52% | 34.73% |
| Total Mesophiles Germs | <11 | | | |
| Yeast and molds | <11 | | | |
| Particle Size (lazer granulometry) | 0.946 µm | — | — | 1.354 µm |
| Storage Temperature | | 20° C. | | |

TABLE 3

(0.175% w/w at 45° C.):

| | T0 month | T1 month | T2 months | T3 months |
|---|---|---|---|---|
| General Aspect | Cream | Cream + slight sedimentation | Cream + slight sedimentation | Cream + slight sedimentation |
| Color | White | White | White | White |
| pH | 5.55 | 5.49 | 5.46 | 5.42 |
| Dry Matter 105° C. | 32.00% | 29.52% | 32.48% | 34.21% |
| Total Mesophiles Germs | <11 | | | |
| Yeast and molds | <11 | | | |
| Particle Size (lazer granulometry) | 0.946 µm | — | — | 1.154 µm |
| Storage Temperature | | 45° C. | | |

Conclusion: After three months at storage temperature 4° C., 20° C. and 45° C., it appears that vesicles of the invention (SPHERULITES™ loaded wish 0.175% w/w NASHA™) are stable.

They have a slight sedimentation which is usual for this type of SPHERULITES™ vesicles.

The pH, dry matter values and particle size are constant.

2b. Stability of SPHERULITES™ vesicles loaded wish 0.35% w/w NASHA™

TABLE 4

(0.35% w/w at 4° C.):

| | T0 month | T1 month | T2 months | T3 months | T6 months |
|---|---|---|---|---|---|
| General Aspect | Cream | Cream + sedimentation | Cream + sedimentation | Cream + sedimentation | Cream + sedimentation |
| Color | White | White | White | White | White |
| pH | 5.47 | 5.39 | 5.45 | 5.46 | 5.37 |
| Dry Matter 105° C. | 32.54% | 32.91% | 32.63% | 33.24% | 31.06% |
| Total Mesophiles Germs | <9 | <9 | <10 | 10 | Accurate (<10) |
| Yeast and molds | <9 | <9 | <10 | <10 | Accurate (<10) |
| Particle Size (lazer granulometry) | 0.984 µm | — | — | 1.497 µm | 1.107 µm |
| Storage Temperature | | | 4° C. | | |

TABLE 5

(0.35% w/w at 20° C.):

| | T0 month | T1 month | T2 months | T3 months | T6 months |
|---|---|---|---|---|---|
| General Aspect | Cream | Cream + slight sedimentation | Cream + slight sedimentation | Cream + slight sedimentation | Cream + slight sedimentation |
| Color | White | White | White | White | White |
| pH | 5.47 | 5.42 | 5.44 | 5.43 | 5.37 |
| Dry Matter 105° C. | 32.54% | 32.64% | 32.48% | 33.02% | 32.98% |
| Total Mesophiles Germs | <9 | | | | Accurate (<10) |
| Yeast and molds | <9 | | | | Accurate (<10) |
| Particle Size (lazer granulometry) | 0.984 µm | — | — | 1.025 µm | 0.779 µm |
| Storage Temperature | | | 20° C. | | |

TABLE 6

(0.35% w/w at 45° C.):

| | T0 month | T1 month | T2 months | T3 months | T6 months |
|---|---|---|---|---|---|
| General Aspect | Cream | Cream + slight sedimentation | Cream + slight sedimentation | Cream + slight sedimentation | Milk (sedimentation) |
| Color | White | White | White | White | Yellowish |
| pH | 5.47 | 5.35 | 5.35 | 5.33 | 4.80 |
| Dry Matter 105° C. | 32.54% | 33.30% | 32.69% | 33.35% | 34.72% |
| Total Mesophiles Germs | <9 | | | | Accurate (<10) |
| Yeast and molds | <9 | | | | Accurate (<10) |
| Particle Size (lazer granulometry) | 0.984 µm | — | — | 0.696 µm | 0.817 µm |
| Storage Temperature | | | 45° C. | | |

Conclusion: After three months at storage temperature 4° C., 20° C. and 45° C., it appears that vesicles of the invention (SPHERULITES™ loaded wish 0.35% w/w NASHA™) are stable.

They have a slight sedimentation which is usual for this type of SPHERULITES™ vesicles.

The pH, dry matter values and particle size are constant.

2c. Stability of SPHERULITES™ vesicles loaded wish 0.5% w/w NASHA™

TABLE 7

(0.5% w/w at 4° C.):

| | T0 month | T1 month | T2 months | T3 months | T6 months |
|---|---|---|---|---|---|
| General Aspect | Cream | Cream + slight sedimentation | Cream + sedimentation | Cream + sedimentation | Cream + sedimentation |
| Color | White | White | White | White | White |
| pH | 5.38 | 5.44 | 5.37 | 5.45 | 5.35 |
| Dry Matter 105° C. | 34.47% | 33.28% | 33.72% | 33.82% | 29.35% |
| Total Mesophiles Germs | <6 | <9 | <9 | <9 | Accurate (<10) |
| Yeast and molds | <6 | <9 | <9 | <9 | Accurate (<10) |
| Particle Size (lazer granulometry) | 0.363 µm | — | — | 0.871 µm | 0.897 µm |
| Storage Temperature | | | 4° C. | | |

TABLE 8

(0.5% w/w at 20° C.):

| | T0 month | T1 month | T2 months | T3 months |
|---|---|---|---|---|
| General Aspect | Cream | Cream + slight sedimentation | Cream + slight sedimentation | Cream + slight sedimentation |
| Color | White | White | White | White |
| pH | 5.38 | 5.48 | 5.40 | 5.36 |
| Dry Matter 105° C. | 34.47% | 35.38% | 33.11% | 32.87% |
| Total Mesophiles Germs | <6 | | | |
| Yeast and molds | <6 | | | |
| Particle Size (lazer granulometry) | 0.363 μm | — | — | 0.605 μm |
| Storage Temperature | | 20° C. | | |

TABLE 9

(0.5% w/w at 45° C.):

| | T0 month | T1 month | T2 months | T3 months |
|---|---|---|---|---|
| General Aspect | Cream | Cream | Cream + slight sedimentation | Cream + slight sedimentation |
| Color | White | White | White | White |
| pH | 5.38 | 5.43 | 5.35 | 5.26 |
| Dry Matter 105° C. | 34.47% | 32.79% | 32.75% | 32.95% |
| Total Mesophiles Germs | <6 | | | |
| Yeast and molds | <6 | | | |
| Particle Size (lazer granulometry) | 0.363 μm | — | — | 0.735 μm |
| Storage Temperature | | 45° C. | | |

Conclusion: After three months at storage temperature 4° C., 20° C. and 45° C., it appears that vesicles of the invention (SPHERULITES™ loaded wish 0.5% w/w NASHA™) are stable.

They have a slight sedimentation which is usual for this type of SPHERULITES™ vesicles.

The pH, dry matter values and particle size are constant.

Example 3

Composition Sheet of a Vesicle According to the Invention: NASHA™ Loaded into and/or onto SPHERULITES™ Vesicles

TABLE 10

| INCI (US) | % Amount (w/w) | % Amount (w/w) | % Amount (w/w) |
|---|---|---|---|
| Water | qsp 100 | Qsp 100 | Qsp100 |
| Sucrose palmitate | 20 | 20 | 20 |
| Tocopheryl acetate | 6.75 | 6.75 | 6.75 |
| Glyceryl linoleate | 5.00 | 5.00 | 5.00 |
| Sodium hyaluronate crosspolymer-2 | 0.175 | 0.35 | 0.5 |
| Phenoxyethanol | 1.00 | 1.00 | 1.00 |
| Potassium sorbate | 0.50 | 0.50 | 0.50 |
| Citric acid | qs pH 5 | qs pH 5 | qs pH 5 |

Example 4

Gel According to the Invention

| Ingredients | Range amount (% w/w) |
|---|---|
| Purified water | 65-80% |
| Thickening agent | 2-5% |
| NASHA SPHERULITES ™ | 1-3% |
| Humectants/Hydratants | 8-15% |
| Skin protectants | 5-10% |
| Preservatives | 0.5-1% |

Example 5

SPF30 Moisturizer According to the Invention

| Ingredients | Range amount (% w/w) |
|---|---|
| Purified water | 45-55% |
| Emulsifiers | 3-5% |
| Thickening agent | 0.5-3% |
| Emollients | 8-15% |
| Mineral sunscreens | 8-12% |
| Organic sunscreens | 9-13% |
| NASHA SPHERULITES ™ | 1-3% |
| Humectants/Hydratants | 1-5% |
| Skin protectants | 4-7% |
| Preservatives | 0.5-1% |

Example 6

SPF20 Lip Balm According to the Invention

| Ingredients | Range amount (% w/w) |
|---|---|
| Purified water | 1-5% |
| Waxes | 40-60% |
| Mineral sunscreens | 5-8% |
| Organic sunscreens | 7-10% |
| NASHA SPHERULITES ™ | 1-3% |
| Emollients | 2-5% |
| Skin protectants | 5-7% |

Example 7

Characterization of Spherulites Technology

Raman microspectrometry confirms that the Cross linked HA is combined onto the SPHERULITES™ vesicles.

The invention claimed is:

1. A micro- or nanoparticular vesicle comprising at least a crosslinked hyaluronic acid, wherein:
   (a) the micro- or nanoparticular vesicle is a multilamellar vesicle comprising concentric membranes, comprising at least one non-ionic surfactant of the sucrose ester type, comprising at least one chain arising from a linear or branched, saturated or unsaturated, optionally mono- or polyhydroxylated, $C_{12}$ to $C_{22}$ fatty acid;
   (b) the crosslinked hyaluronic acid is crosslinked by a chemical crosslinking agent; has a degree of modification of the crosslinked hyaluronic acid with the chemical crosslinking agent that is less than 1.9 mole %; and is loaded onto the vesicle and/or into the vesicle at a concentration between 0.01% and 5% (w/w).

2. The micro- or nanoparticular vesicle according to claim 1, wherein the degree of modification of the crosslinked hyaluronic acid with the chemical crosslinking agent is between 0.1 and 1.9 mole %.

3. The micro- or nanoparticular vesicle according to claim 1, wherein the degree of modification of the crosslinked hyaluronic acid with the chemical crosslinking agent is about 1.0 mole %.

4. The micro- or nanoparticular vesicle according to claim 1, wherein the chemical crosslinking agent is a bi- or polyfunctional crosslinking agent comprising two or more glycidyl ether functional groups.

5. The micro- or nanoparticular vesicle according to claim 1, wherein the crosslinked hyaluronic acid is sodium hyaluronate crosspolymer-2.

6. The micro- or nanoparticular vesicle according to claim 1, wherein the vesicle is prepared from the mixture of a monoester of polyoxyethylene fatty acids, cholesterol, and free fatty acids.

7. The micro- or nanoparticular vesicle according to claim 1, wherein the crosslinked hyaluronic acid is loaded onto the vesicle and/or into the vesicle at a concentration of 0.175%, 0.35%, or 0.5% (w/w).

8. The micro- or nanoparticular vesicle according to claim 1, wherein the crosslinked hyaluronic acid is loaded onto the micro- or nanoparticular vesicle.

9. The micro- or nanoparticular vesicle according to claim 1, further comprising a non-crosslinked hyaluronic acid, wherein up to 50% by weight of the total hyaluronic acid in the vesicle is non-crosslinked.

10. A composition comprising a micro- or nanoparticular vesicle according to claim 1, in a physiologically acceptable medium.

11. The composition according to claim 10, wherein the concentration of the vesicle is between 0.1% and 10% by weight, relative to the total weight of the composition.

12. The composition according to claim 10, wherein the concentration of the vesicle is about 1%, about 2%, or about 3% by weight, relative to the total weight of the composition.

13. The composition according to claim 10, wherein the vesicles are cationic vesicles, non-ionic vesicles, or a combination thereof.

14. The composition according to claim 10, wherein the composition is formulated for topical and/or parenteral application.

15. A method of manufacturing a micro- or nanoparticular vesicle, comprising:
   (a) preparing a non-ionic surfactant phase containing the non-ionic surfactants;
   (b) preparing an aqueous phase containing the crosslinked hyaluronic acid;
   (c) mixing the aqueous phase into the non-ionic surfactant phase with a controlled stirring and heating mode to form a preparation containing the vesicles comprising surfactant bi-layers; and
   (d) diluting the preparation containing the vesicles with water;
   wherein:
      (i) the micro- or nanoparticular vesicle is a multilamellar vesicle comprising concentric membranes, comprising at least one non-ionic surfactant of the sucrose ester type, comprising at least one chain arising from a linear or branched, saturated or unsaturated, optionally mono- or polyhydroxylated, $C_{12}$ to $C_{22}$ fatty acid;
      (ii) the crosslinked hyaluronic acid is crosslinked by a chemical crosslinking agent; has a degree of modification of the crosslinked hyaluronic acid with the chemical crosslinking agent that is less than 1.9 mole %; and is loaded onto the vesicle and/or into the vesicle at a concentration between 0.01% and 5% (w/w).

16. The method according to claim 15, wherein the crosslinked hyaluronic acid is loaded onto the vesicles.

17. A method of caring for skin or reducing the effects of skin ageing, comprising topically applying a composition according to claim 10 to the skin of a human subject in need thereof.

* * * * *